(12) United States Patent
Simard

(10) Patent No.: US 9,724,409 B2
(45) Date of Patent: *Aug. 8, 2017

(54) TREATMENT OF INFLAMMATORY SKIN DISEASE

(71) Applicant: XBiotech, Inc., Vancouver (CA)

(72) Inventor: John Simard, Austin, TX (US)

(73) Assignee: XBiotech, Inc., Vancouver (CA)

( * ) Notice: Subject to any disclaimer, the term of this patent is extended or adjusted under 35 U.S.C. 154(b) by 627 days.

This patent is subject to a terminal disclaimer.

(21) Appl. No.: 13/644,976

(22) Filed: Oct. 4, 2012

(65) Prior Publication Data

US 2013/0039921 A1    Feb. 14, 2013

Related U.S. Application Data

(63) Continuation-in-part of application No. 13/437,159, filed on Apr. 2, 2012, now abandoned.

(60) Provisional application No. 61/470,538, filed on Apr. 1, 2011.

(51) Int. Cl.
*A61K 39/395* (2006.01)
*C07K 16/24* (2006.01)
*A61K 39/00* (2006.01)

(52) U.S. Cl.
CPC .......... *A61K 39/395* (2013.01); *C07K 16/245* (2013.01); *A61K 2039/505* (2013.01)

(58) Field of Classification Search
None
See application file for complete search history.

(56) References Cited

U.S. PATENT DOCUMENTS

| | | | |
|---|---|---|---|
| 2002/0022720 A1 | 2/2002 | Le | |
| 2003/0026806 A1* | 2/2003 | Witte et al. | 424/145.1 |
| 2005/0276807 A1* | 12/2005 | Skurkovich et al. | 424/145.1 |
| 2009/0215992 A1 | 8/2009 | Wu | |
| 2009/0298096 A1* | 12/2009 | Simard | 435/7.21 |

FOREIGN PATENT DOCUMENTS

| | | |
|---|---|---|
| WO | 9524917 | 9/1995 |
| WO | 2012034039 | 3/2012 |

OTHER PUBLICATIONS

Kurokawa et al., Experimental Dermatology, 18, 821-832, 2009.*
Bonifati, C. et al.: "IL-1alpha, IL-1beta and psoriasis: conflicting results in the literature. Opposite behaviour of the two cytokines in lesional or non-lesional extracts of whole skin," Journal of Biological Regulators and Homeostatic Agents, Oct. 1997, vol. 11, No. 4:133-136.
Gonzalez-Lopez, M.A. et al: "New-onset psoriasis following treatment with the interleukin-1 receptor antagonist anakinra," British Journal of Dermatology, May 2008, vol. 158, No. 5:1146-1148.
Yost, J. and J.E. Gudjonsson: "The role of TNF inhibitors in psoriasis therapy: new implications for associaed comorbidities," Medicine Reports, May 2009, vol. 1, No. 30:1-4.
Hoge, E.A. et al: "Broad spectrum of cytokine abnormalities in panic disorder and posttraumatic stress disorder," Depression and Anxiety, May 2009, vol. 26, Issue 5: 447-455;Abstract only.
Saitta, P. et al: "An Update on the Presence of Psychiatric Comorbidities in Acne Patients, Part 2: Depression, Anxiety, and Suicide," CUTIS, Aug. 2011, vol. 88:92-97.
Carrasco, Daniel et al: "An Open Label, Phase 2 Study of MABp1 Monotherapy for the Treatment of Acne Vulgaris and Psychiatric Comorbidity," Journal of Drugs in Dermatology, Jun. 2015, vol. 14, Issue 6: 560-564.
Grahame, V. et al: "The Psychological Correlates of Treatment Efficacy in Acne," Dermatol Psychosom, 2002, vol. 3:119-125.
Rubinow, David R. et al: "Reduce anxiety and depression in cystic acne patients after successful treatment with oral isotretinoin," Journal of the American Academy of Dermatology, 1987, vol. 17, No. 1:25-32.
Kaymak, Yesim et al: "Comparison of depression, anxiety and life quality in acne vulgaris patients who were treated with either isotretinoin or topical agents, The International Society of Dermatology," 2009, vol. 48:41-46.
Dinarello, Charles A. et al: "Treating inflammation by blocking interleukin-1 in a broad spectrum of diseases," Nature Reviews/Drug Discovery, Aug. 2012, vol. 11: 633-652.
Rossi, Silvia et al: "Interleukin-1 beta Causes Anxiety by Interacting with the Endocannabinoid System," The Journal of Neuroscience, Oct. 2012, vol. 32, No. 40:13896-13905.
Szabo, K. et al: "Interleukin-1A +4845(G>T) polymorphism is a factor predisposing to acne vulgaris," Tissue Antigens, 2010, vol. 76:411-415.

* cited by examiner

*Primary Examiner* — Marianne P Allen
(74) *Attorney, Agent, or Firm* — Stanley A. Kim

(57) ABSTRACT

The number of acne lesions in a human subject is reduced by administering to the subject a pharmaceutical composition that includes a pharmaceutically acceptable carrier and a therapeutically effective amount of an agent that selectively binds IL-1α. Anxiety and other psychiatric conditions are also improved with this treatment.

11 Claims, No Drawings

TREATMENT OF INFLAMMATORY SKIN DISEASE

CROSS-REFERENCE TO RELATED APPLICATIONS

This application is a continuation-in-part application of U.S. patent application Ser. No. 13/437,159 filed on Apr. 2, 2012, which claims priority from U.S. provisional patent application No. 61/470,538 filed on Apr. 1, 2011.

STATEMENT AS TO FEDERALLY SPONSORED RESEARCH

Not applicable.

FIELD OF THE INVENTION

The invention relates generally to the fields of medicine, dermatology, and immunology. More particularly, the invention relates to the use of antibodies (Abs) which specifically bind interleukin-1α (IL-1α) to treat inflammatory skin diseases as well as psychiatric conditions.

BACKGROUND

Inflammatory skin disorders acne, rosacea, and psoriasis afflict many millions of people. While not usually lethal, these conditions can cause physical discomfort and affect emotional well-being. There are currently a large number of different treatments for inflammatory skin disorders including corticosteroids, vitamin D analogs, coal tar, ultraviolet light, retinoids, methotrexate, cyclosporine, hydroxyurea, antibiotics, and biologic agents such as TNFalpha inhibitors. While these therapies have proven useful for many patients, many cause undesirable side-effects and none are ideal for every situation.

SUMMARY

The invention is based on the discovery that a mAb that specifically binds IL-1α is useful for treating acne vulgaris and various psychiatric conditions (such as anxiety and poor self-image).

Accordingly, the invention features a method of reducing the number of acne lesions in a human subject, as well as a method of treating a psychiatric condition (e.g., anxiety, depression, or poor self-image) in a human subject. These methods can include the step of administering to the subject a pharmaceutical composition including a pharmaceutically acceptable carrier and an amount of an agent that selectively binds IL-1α effective to reduce to reduce the number of acne lesions or improve a psychiatric condition in the subject. The agent can be an anti-IL-1α antibody such as a monoclonal antibody (e.g., of the IgG1 isotype), a monoclonal antibody that includes a complementarity determining region of MABp1, or MABp1.

Another aspect of the invention features a method of reducing skin inflammation in a human subject by administering to the subject a pharmaceutical composition including a pharmaceutically acceptable carrier and an amount of an anti-IL-1α Ab (or other agent that specifically and/or selectively binds IL-1α) effective to reduce a symptom of skin inflammation (e.g., redness, swelling, leukocyte infiltration, lesion development, or lesion number) in the subject by at least about 10% (e.g., at least 8, 9, 10, 15, 17, 20, 30, 40, 50, 60, 70, 80, 90, or 100%) as measured by any standard dermatological test. The anti-IL-1α Ab can be a mAb such as an IgG1. The anti-IL-1α Ab can be the mAb designated as MABp1 or a mAb that includes one or more complementarity determining regions (CDRs) of MABp1. The pharmaceutical composition can be administered to the subject by injection, subcutaneously, intravenously, intramuscularly, or intradermally. In the method, the dose can be at least 0.25 (e.g., at least 0.2, 0.5, 0.75, 1, 2, 3, 4, or 5) mg/ml.

In other aspects, the invention includes use of an agent that selectively binds IL-1α to treat acne and/or a psychiatric condition in the subject, and a pharmaceutical composition for treating acne and/or a psychiatric condition in the subject, the composition comprising an agent that selectively binds IL-1α. In the foregoing, the agent can be an anti-IL-1α antibody such as a monoclonal antibody (e.g., of the IgG1 isotype), or a monoclonal antibody that includes a CDR of MABp1, or MABp1.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, $27^{th}$ Edition, Lippincott, Williams & Wilkins, 2000.

As used herein, an "antibody" or "Ab" is an immunoglobulin (Ig), a solution of identical or heterogeneous Igs, or a mixture of Igs. An "Ab" can also refer to fragments and engineered versions of Igs such as Fab, Fab', and $F(ab')_2$ fragments; and scFv's, heteroconjugate Abs, and similar artificial molecules that employ Ig-derived CDRs to impart antigen specificity. A "monoclonal antibody" or "mAb" is an Ab expressed by one clonal B cell line or a population of Ab molecules that contains only one species of an antigen binding site capable of immunoreacting with a particular epitope of a particular antigen. A "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule. An Ab that "selectively binds" a first molecule specifically binds the first molecule at a first epitope but does not specifically bind other molecules that do not have the first epitope. For example, an Ab which selectively binds IL-1alpha specifically binds an epitope on IL-1alpha but does not specifically bind IL-1beta (which does not have the epitope).

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All applications and publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses compositions and methods for reducing skin inflammation including ameliorating one or more symptoms of a dermatological pathology in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein. Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, 49th Edition, McGraw-Hill Medical, 2010; and Fauci et al., Harrison's Principles of Internal Medicine, 17th Edition, McGraw-Hill Professional, 2008. Methods in dermatology are described in James et al., Andrews' Diseases of the Skin: Clinical Dermatology—Expert Consult, 11th Ed., Saunders, 2011; and Burns et al., Rook's Textbook of Dermatology, 8th Ed., Wiley-Blackwell, 2010.

Treatment

The compositions and methods described herein are useful for treating skin inflammation (e.g., associated with rosacea, eczema, psoriasis, xerosis, dermatitis, acne, pyoderma gangrenosum, urticaria, lichenoid disorders, bullous diseases such as bullous pemphigoid, cutaneous vasculitis, and granulomatous skin diseases) as well as psychiatric conditions (e.g., anxiety, depression, and poor self image) in a mammalian subject by administering to the subject a pharmaceutical composition including an amount of an anti-IL-1α Ab effective to improve at least one characteristic of the inflammation (e.g., reduction in the number or size of lesions, reduction of redness, and reduction in itchiness) or psychiatric condition in the subject. The mammalian subject might be any that suffers from skin inflammation or a psychiatric condition including, human beings, dogs, cats, horses, cattle, sheep, goats, and pigs. Human subjects might be male, female, adults, children, seniors (65 and older), and those with other diseases. Particularly preferred subjects are those whose disease has progressed or failed to respond after treatment with other anti-inflammatory or anti-microbial agents such as retinoids, antibiotics, steroids or cytokine inhibitors such as TNFalpha inhibitors. Subjects who have developed a human anti-human antibody response due to prior administration of therapeutic antibodies are preferred when the anti-IL-1α Ab is a true human Ab (e.g., one that is naturally expressed in a human subject) such as MABp1. Any type of inflammatory skin disease susceptible to treatment with an anti-IL-1α Ab might be targeted. Anti-IL-1α Ab administration is thought to be particularly effective for treating acne vulgaris and psoriasis vulgaris.

Antibodies and Other Agents that Target IL-1α

Any suitable type of Ab that specifically binds IL-1α and reduces a characteristic of a psychiatric condition, skin inflammation and/or an inflammatory skin disease such as acne vulgaris or psoriasis vulgaris in a subject might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1 \times 10^9$ $M^{-1}$ or greater (e.g., greater than $9 \times 10^{10}$ $M^{-1}$, $8 \times 10^{10}$ $M^{-1}$, $7 \times 10^{10}$ $M^{-1}$, $6 \times 10^{10}$ $M^{-1}$, $5 \times 10^{10}$ $M^{-1}$, $4 \times 10^{10}$ $M^{-1}$, $3 \times 10^{10}$ $M^{-1}$, $2 \times 10^{10}$ $M^{-1}$, or $1 \times 10^{10}$ $M^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. patent application Ser. No. 12/455,458 filed on Jun. 1, 2009. Other useful mAbs are those that include at least one but preferably all the CDRs of MABp1.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "FACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, MAbs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and E. coli cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, mAbs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the human IL-1α mAbs might be conjugated with another molecule such as a cytotoxin. A human IL-1α specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, and $^{211}At$), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), Pseudomonas exotoxin (PE) A, PE40, abrin, saporin, pokeweed viral protein, ethidium bromide, glucocorticoid, anthrax toxin and others. See, e.g., U.S. Pat. No. 5,932,188.

While the IL-1α specific Abs described above are preferred for use in the invention, in some cases, other agents that specifically target IL-1α might be used so long as their administration leads to improvement of a characteristic of an inflammatory skin disease and/or a psychiatric condition. These other agents might include vaccines that cause the production of anti-IL-1α Abs, proteins or peptides that bind IL-1α, and small organic molecules which specifically target IL-1α. Those that do not specifically bind other agents that specifically target IL-1β are preferred.

Pharmaceutical Compositions and Methods

The anti-IL-1α Ab compositions (and other agents that specifically target IL-1α) may be administered to animals or humans in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent.

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., the skin) by, for example, topical application. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in patients as measured by the improvement in one or more symptoms of skin inflammation. As is well known in the medical arts, dosage for any one animal or human depends on many factors, including the subject's size, body surface area, age, the particular composition to be administered, sex, time and route of administration, general health, and other drugs being administered concurrently. Preferred doses range from about 0.1 to 5 (e.g., 0.05, 0.1, 0.15, 0.2, 0.3, 0.4, 0.5, 1, 2, 3, 4, 5, or 6) mg/kg body weight. In some cases a single dose is effective at resolving an episode of skin inflammation. In other cases, doses may be given repeatedly, e.g., semi-weekly, weekly, bi-weekly, tri-weekly, semi-monthly, once every three weeks, monthly, bi-monthly, or as needed (if skin inflammation recurs).

EXAMPLES

Example 1—Xilonix™

Xilonix™ is a sterile injectable liquid formulation of 15 mg/mL MABp1 in a stabilizing isotonic buffer (pH 6.4). Each 10-mL Type I borosilicate glass serum vial contains 5 mL of the formulation, and is sealed with a 20-mm Dalkyo Fluorotec butyl rubber stopper and flip-off aluminum seal. The product is stored at 5±3° C., with excursions to room temperature permitted. The exact composition of the drug product is shown below:

| Composition of the Drug Product (Xilonix ™) | | | |
|---|---|---|---|
| Ingredient | Grade | Manufacturer | Concentration |
| MABp1 Ab | GMP | XBiotech | 15 mg/mL |
| sodium phosphate dibasic | compendial | J T Baker | 12 mg/mL |
| citric acid monohydrate | compendial | J T Baker | 2 mg/mL |
| Trehalose•2H2O (high-purity low endotoxin) | compendial | Ferro-Pfanstiehl | 60 mg/mL |
| polysorbate 80 | compendial | J T Baker | 0.2 mg/mL |
| Phosphoric acid, to adjust pH | compendial | J T Baker | 0.04 mg/mL |
| water for injection | compendial | Microbix | q.s. |

Method of Administration:

The calculated volume is withdrawn from the drug (mAb)-containing vial(s) using a suitable syringe. The drug is then injected into a subject subcutaneously.

Example 2—Treatment of Acne Vulgaris

An 18-year-old male presented with moderate-to-severe acne vulgaris affecting his arms, back, chest and face. There was significant induration of the lesions, particularly on the back. The patient described this as an acute outbreak but reported ongoing acne vulgaris problems since 15 years of age. Topical retinoids and corticosteroids had been used in the past with some degree of effectiveness. Also limited UV treatment, by use of tanning beds, had been used with limited results. The patient was given a single 3 ml subcutaneous injection of Xilonix™ (MABp1; 15 mg/ml), representing a dose of 0.6 mg/kg.

The patient was observed for 2 hours post-infusion. There was no apparent infusion reaction, or adverse response to the drug. After 24-hours the patient was re-evaluated. Large lesions on the shoulder and back had dramatically reduced in size. Reduced inflammatory infiltration of facial lesions was evidenced by less redness of the lesions and reduced lesion sizes compared to pre-dose. The lesions appeared to be drying.

After 72-hours the patient was re-examined. The improvement was remarkable. Most lesions showed dramatically less inflammation or many were altogether non-apparent. Lesions on shoulder and back that had remarkable induration were resolved, only slightly discolored and soft to the touch. The patient's face looked essentially normal and the patient remarked that he was very happy with the appearance of his skin. One week after injection the patient showed continued improvement and all areas of skin appeared without notable lesions.

Example 3—Formulation of MABp1 for Subcutaneous Injection

T2-18C3 is a sterile liquid formulation of 100±5 mg/mL MABp1 in a stabilizing isotonic formulation buffer (pH 6.4±0.1). 1.4±0.1 mL of this formulation was contained within two mL Type I borosilicate glass serum vials sealed with a 20-mm Dalkyo Fluorotec butyl rubber stopper and flip-off aluminum seal. The product with stored upright at 5±3° C., with excursions to room temperature permitted. The exact composition of the Drug Product is shown below in Table 2:

TABLE 2

Composition of T2-18C3 Drug Product

| Ingredient | Grade | Manufacturer | Concentration |
| --- | --- | --- | --- |
| MABp1 antibody | GMP | XBiotech USA Inc | 100 mg/mL |
| trehalose•2H2O | GMP, High purity, Low endotoxin | Ferro-Pfanstiehl (USA) | 60 mg/mL |
| sodium phosphate dibasic | GMP, EP, USP, JP | J T Baker (USA) | 12 mg/mL |
| citric acid monohydrate | GMP, EP, USP, BP | J T Baker (USA) | 2 mg/mL |
| polysorbate 80 | GMP, EP, NF, JP | J T Baker (USA) | none |
| sterile water for injection | GMP, EP, USP | Microbix (Canada) | q.s. |

Example 4—Treatment of Psoriasis

A 48-year old male with a history of Type I psoriasis vulgaris, diagnosed at age 5 was treated with T2-18C3. The patient has a positive family history of psoriasis vulgaris, with his sibling, father, and grandmother being affected as well. He was previously treated with topical retinoids and vitamin D3 preparations with minimal improvement. Previous treatment with topical steroids and UV treatment showed benefit. Prior to administration of T2-18C3, the patient had no history of treatment with biologic agents.

The patient was administered 2 subcutaneous injections of MABp1 in the lower abdomen (a total of 160 mg MABp1) on day 0. The patient tolerated the injections well, and there were no complications. The patient's back was evaluated at 17 hours, 41 hours, 5 days, 6 days and 10 days post-administration. At 17 hours, a modest improvement in the redness associated with the lesions was observed. At 41 hours continued improvement was noted with a clearly observable decrease in the size and redness of the lesions. By day 5, significant resolution of the lesions was observed. This improvement continued through day 6. The lesions were almost completely resolved by day 10.

Example 5—Treatment of Psoriasis

An open label trial of the True Human™ monoclonal antibody RA-18C3 (specific for IL-1alpha) was conducted in human subjects with moderate to severe plaque psoriasis. Trial subjects receive 200 mg of RA-18C3 via subcutaneous injection at Days 0, 21, and 42 for a total of 3 injections. PASI (Psoriasis Area and Severity Index Assessment) scores were obtained for each subject at different time points. All of the first five evaluable subjects study showed a decrease in PASI score (i.e., improvement of the disease) at day 56. The mean reduction in PASI scores of the first five evaluable subjects at day 56 was almost 50%.

Example 6: Interim Results of A Phase II Open Label Study of the Safety, Pharmacokinetics, and Efficacy of a True Human™ Anti-Inflammatory Therapeutic Antibody (RA-18C3) in Subjects with Moderate to Severe Acne Vulgaris RA-18C3 is a sterile injectable liquid formulation of MABp1 in a stabilizing isotonic buffer. The research population consists of subjects ≥18 years of age, with moderate to severe acne vulgaris. Subjects had an Investigator's Global Assessment of ≥3, ≥15 inflammatory facial lesions, and were candidates for systemic therapy. 11 patients were enrolled. Seven of the 11 enrolled subjects who had lesion count data available for day 56 are included in the analysis. Most patients (86%) were Caucasian, median age was 23 (19-30) years, 5 (71%) were female. The total facial inflammatory lesion count showed an average improvement of 35±8% (median 34%, range 25-48%) on day 42; and 44±23% (median 42%, range 19-71%) on day 56.

The Body Image Disturbance Questionnaire (BIDQ) is a self-administered, clinically validated questionnaire used to assess "negative body image". The internal consistency, reliability and validity of the 7-item Body Image Disturbance Questionnaire has been established by several prior studies, as well as its potential utility in clinical contexts for qualitative analysis. Recently a modified version of the BIDQ was validated specifically for use in patients with acne vulgaris. Self-reported measures of Modified Body Image Disturbance Questionnaire, collected on Day 0 (D0) and Day 21 (D21), were analyzed. This 7-item survey tool assessed different facets of the body image construct, including appearance related concerns, mental preoccupation with those concerns, and resulting impairment of social and occupational functioning. Responding to the first question of BIDQ survey, all 7 subjects reported that acne is their primary skin problem and they are concerned about the appearance of skin. At D21, 43% showed improvement in Mental Preoccupation (Q2), Emotional Distress (Q3), and Social/occupational impairment (Q4); while 86% showed stabilization with no further worsening in Interference with social life (Q5), Interference with school/job (Q6), and Avoidance of activities due to acne problem (Q7). The mean score of the six BIDQ items (Q2 to Q7) showed marked reduction at D21 from the D0 level, which indicates an across the board improvement in the body image disturbance.

It has been hypothesized that a causal relationship exists between underlying inflammatory processes present in skin diseases and psychiatric medical conditions. To further explore this possibility, the Hospital Anxiety and Depression Scale (HADS) was used to assess the depression and anxiety profiles of the trial population. D0 and D21 scores were available for all the 7 subjects. The mean anxiety score on D0 and D21 were 6.1±3.1 (median 6.0) and 3.3±3.9 (median 3), respectively (Δ 2.9) (Figure 3). As observed from high D0 scores, considerable level of baseline anxiety was prevalent in the study population (median 6). It is important to note that about 50% reduction (from 6.1±3.1 to 3.3±3.9) in anxiety was achieved by D21. The subjects showing ≥3 point improvement in anxiety score had a substantial (21% to 34%) reduction in "facial inflammatory lesion count" on D21. Mean depression score was 2.6±3.1 (median 1) and 2.1±3.1 (1) on D0 and D21, respectively.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of reducing the number of acne lesions in a human subject with acne, the method comprising the step of administering to the subject a pharmaceutical composition comprising a pharmaceutically acceptable carrier and an amount of an anti-IL-1α antibody effective to reduce the number of acne lesions in the subject, wherein the number of acne lesions in the subject is reduced after the step of administering the pharmaceutical composition and at least some of the lesions are resolved within 72 hours after the step of administering the pharmaceutical composition.

2. The method of claim 1, wherein the anti-IL-1α antibody is a monoclonal antibody.

3. The method of claim 2, wherein the monoclonal antibody is an IgG1.

4. The method of claim 2, wherein the monoclonal antibody comprises a complementarity determining region of MABp1.

5. The method of claim 2, wherein the monoclonal antibody is MABp1.

6. The method of claim 1, wherein the step of administering the pharmaceutical composition is performed by subcutaneous injection.

7. A method of reducing the number of acne lesions in a human subject with acne, the method comprising the step of administering to the subject a pharmaceutical composition comprising a pharmaceutically acceptable carrier and an amount of anti-IL-1α antibody effective to reduce the number of acne lesions in the subject, wherein the number of acne lesions in the subject is reduced by at least 35% by the forty-second day after the step of administering the pharmaceutical composition.

8. The method of claim 7, wherein the anti-IL-1α antibody is a monoclonal antibody.

9. The method of claim 8, wherein the monoclonal antibody is an IgG1.

10. The method of claim 8, wherein the monoclonal antibody comprises a complementarity determining region of MABp1.

11. The method of claim 8, wherein the monoclonal antibody is MABp1.

* * * * *